United States Patent [19]
de Boer

[11] Patent Number: 5,179,110
[45] Date of Patent: Jan. 12, 1993

[54] 5-ISOTHIAZOLAMINE DERIVATIVES

[75] Inventor: Thijs de Boer, Oss, Netherlands

[73] Assignee: Akzo N.V., Arnhem, Netherlands

[21] Appl. No.: 725,157

[22] Filed: Jul. 3, 1991

[30] Foreign Application Priority Data

Jul. 3, 1990 [EP] European Pat. Off. ........... 90307246

[51] Int. Cl.$^5$ .................. C07D 417/04; A61K 31/41
[52] U.S. Cl. .................................. 514/326; 514/342; 546/209; 546/280
[58] Field of Search .............. 546/280, 209; 514/342, 514/326

[56] References Cited

U.S. PATENT DOCUMENTS

| | | | |
|---|---|---|---|
| 4,650,805 | 3/1987 | Jaen | 514/326 |
| 4,866,077 | 9/1989 | Bogeso | 514/326 |
| 5,053,416 | 10/1991 | Toja | 514/340 |

Primary Examiner—Robert Gerstl
Attorney, Agent, or Firm—Donna Bobrowicz; William M. Blackstone

[57] ABSTRACT

The invention relates to 5-isothiazolamine derivatives having the formula

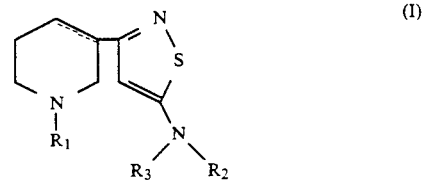

in which $R_1$ is hydrogen, methyl, or ethyl, $R_2$ and $R_3$ are independently selected from hydrogen and alkyl, and the dotted line represents an optional bond, or a pharmaceutically acceptable acid addition salt thereof.

The compounds have $\alpha_2$-adrenergic agonistic properties with little cardiovascular side-effects and minimal or no dopaminergic and cholinergic activity.

6 Claims, No Drawings

5-ISOTHIAZOLAMINE DERIVATIVES

The invention relates to 5-isothiazolamine derivatives having the formula (I)

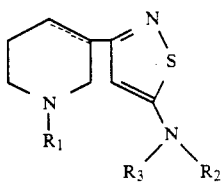

in which $R_1$ is hydrogen, methyl, or ethyl, $R_2$ and $R_3$ are independently selected from hydrogen and alkyl, and the dotted line represents an optional bond, or a pharmaceutically acceptable acid addition salt thereof, as well as to a process for the preparation thereof and to pharmaceutical compositions containing the same.

The compounds of this invention have $\alpha_2$-adrenergic agonistic properties with little cardiovascular sideeffects and minimal or no dopaminergic and cholinergic activity, and can, for instance, be used for the prevention of gastric acid secretion and gastric ulceration, diarrhea, incontinence, and as bronchodilator, for the treatment of glaucoma, osteoporosis, benign prostate hypertrophy, diabetes, and migraine, and it acts as an adjuvant synergistically with general anesthetics.

The term alkyl in the definition of $R_2$ and $R_3$ means a lower alkyl group with 1-6 carbon atoms and preferably with 1-4 carbon atoms. Examples are methyl, ethyl, propyl, isopropyl, butyl, sec-butyl, pentyl, neo-pentyl, and hexyl. The most preferred alkyl group is the methyl group. The most preferred $R_1$ group is methyl.

A preferred compound according to this invention is the 5-isothiazolamine derivative having the formula

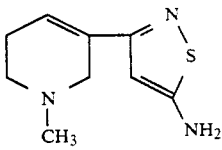

or a pharmaceutically acceptable acid addition salt thereof.

Compounds according to this invention may be prepared by methods known for the preparation of analogous compounds.

A suitable process for the preparation of 5-isothiazolamine derivatives having formula I is, for instance, characterized in that a pyridinium derivative of the formula

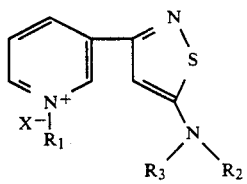

in which $R_1$ is methyl, ethyl, or a protective group, and $R_2$ and $R_3$ have the previously given meanings, or represent a protective group, and $X^-$ is an anion, is reduced, followed by the removal of the protective groups, if present, after which the compound thus obtained may be converted into another compound having formula I, and/or optionally converted into a pharmaceutically acceptable acid addition salt.

Reduction may be performed by methods known for the reduction of pyridinium rings. A suitable method is the reduction with sodium borohydride, optionally followed by reduction with hydrogen in the presence of palladium-charcoal. Compounds having formula I in which the dotted line does not represent a bond may also be prepared by reduction of the pyridinium derivative II using sodium dithionate.

Pyridinium derivative II may be obtained by quaternization of the corresponding pyridinylisothiazolamine derivative with $R_1X$, in which $R_1$ is a methyl or ethyl group, or a suitable protective group such as the phenylmethyl group, and X is a group that gives $X^-$ after quaternization. The pyridinylisothiazolamine derivative may be obtained by condensation of hydrogen sulfide and an aminopyridinylpropenenitrile derivative, followed by cyclization.

The anion $X^-$ is an organic or inorganic anion derived from an acid such as HCl, HBr, HI, $H_2SO_4$, $H_3PO_4$, methanesulphonic acid, and p-toluenesulphonic acid. The preferred anion is $I^-$.

Protective groups are groups that are able to protect reactive functions temporarily. Suitable protective groups are known in the art. Amino groups, for instance, can be protected by phenylmethyl groups or protected as azido groups.

Compounds of formula I in which the dotted line represents a bond can be converted by reduction into compounds of formula I in which the dotted line does not represent a bond. When protective groups are used which are not cleaved during the reduction of the pyridinium group, the protected product must be deprotected. Compounds of formula I may be converted into other compounds of formula I. For instance, compounds of formula I with $R_1$, $R_2$, and/or $R_3$ being hydrogen can be alkylated by for example the method of Leuckart-Wallach, to obtain compounds with $R_1$, $R_2$, and/or $R_3$ being alkyl.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, ascorbic acid, and p-toluenesulphonic acid.

The compounds of this invention may possess a chiral carbon atom, and may therefore be obtained as a pure enantiomer, or as a mixture of enantiomers, among which are the racemic mixture. Methods for obtaining the pure enantiomers are well known in the art, e.g. synthesis with chiral induction, crystallization of salts which are obtained from optically active acids and the racemic mixture, or by chromatographic separation using chiral columns.

The compounds of the invention may be administered enterallyh or parenterally, and for humans preferably in a daily dosage of 0.001 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE a. A solution of 20 g of 3-amino-3-(3-pyridinyl)-2-propenenitrile [J. Med. Chem., 18, 441 (1975)] in 100 ml of pyridine and 14 ml of triethylamine was saturated with hydrogen sulfide and set aside under nitrogen at room temperature for 28 days. The solution was kept saturated by passing hydrogen sulfide into the reaction mixture at intervals during this time. After evaporation the crude product was purified by chromatography and crystallization from ethyl acetate to give 3.65 g of 3-amino-3-(3-pyridinyl)-2-propenethioamide, which was suspended in 80 ml of diethyl ether together with 5.21 g of potassium carbonate. A solution of 5.21 g of iodine in 80 ml of diethyl ether was added dropwise in 10 min to this suspension, keeping the temperature at 3±2° C. After 45 min the reaction mixture was diluted with brine and extracted with dichloromethane. The extract was washed, dried, and evaporated to give 2.19 g of 3-(3-pyridinyl)-5-isothiazolamine.

b. A suspension of 2.19 of 3-pyridinyl)-5-isothiazolamine in 78 ml of acetonitrile containing 2.5 ml of iodomethane was refluxed for 4 h. The mixture was cooled to <10° C. and 1.92 g of 3-(5-aminoisothiazol-3-yl)-1-methylpyridinium iodide was filtered off and dried in vacuo.

c. To a stirred suspension of 1.92 g of 3-(5-aminoisothiazol-3-yl)-1-methylpyridinium iodide in 27 ml of methanol were added portionwise 1.1 g of sodium borohydride, while keeping the temperature <20° C. After dissolution the reaction mixture was diluted with 72 ml of sodium chloride solution and extracted with dichloromethane. The extracts were washed, dried, and evaporated to give 1.24 g of a solid which was dissolved in methanol with a slight excess of a solution of hydrogen chloride in diethyl ether. The product was recrystallized from methanol to give 696 mg of 3-(1,2,5,6-tetrahydro-1-methyl-3-pyridinyl])-5-isothia zolamine dihydrochloride. mp 242° C. (dec.).

I claim:

1. A 5-isothiazolamine derivative comprising the formula

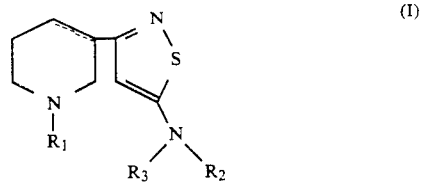

in which $R_1$ is hydrogen, methyl, or ethyl, $R_2$ is selected from the group consisting of hydrogen and a lower alkyl group with 1 to 6 carbon atoms, $R_3$ is selected from the group consisting of hydrogen and a lower alkyl group with 1 to 6 carbon atoms, the dotted line represents an optional bond; or a pharmaceutically acceptable acid addition salt thereof.

2. The 5-isothiazolamine derivative of claim 1 having the formula

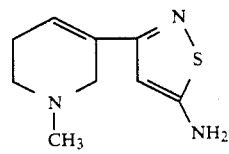

or a pharmaceutically acceptable acid addition salt thereof.

3. A pharmaceutical composition comprising the 5-isothiazolamine derivative of claim 1 in admixture with pharmaceutically acceptable auxiliaries.

4. A 5-isothiazolamine derivative according to claim 1, wherein the lower alkyl group comprises 1 to 4 carbon atoms.

5. A 5-isothiazolamine derivative according to claim 1, wherein the lower alkyl group is methyl.

6. A 5-isothiazolamine derivative according to claim 1, wherein $R_1$ is methyl.

* * * * *